United States Patent [19]

Hardee

[11] Patent Number: 4,676,721
[45] Date of Patent: Jun. 30, 1987

[54] ROOM AIR CLEANER

[76] Inventor: Steve D. Hardee, 4571 SW. 25th Ave., Fort Lauderdale, Fla. 33312

[21] Appl. No.: 876,296

[22] Filed: Jun. 18, 1986

[51] Int. Cl.⁴ .............................................. F04D 29/70
[52] U.S. Cl. .................................. 416/146 R; 416/62; 416/5
[58] Field of Search ............ 416/142 R, 6, 62, 146 R, 416/506; 55/385 R, 385 A, 385 G, 68, 97; 415/121 R

[56] References Cited

U.S. PATENT DOCUMENTS

| | | | |
|---|---|---|---|
| 712,177 | 10/1902 | Bradshaw | 416/146 R |
| 2,033,345 | 3/1936 | Lee | 416/240 X |
| 2,078,197 | 4/1937 | Hooker et al. | 55/385 R |
| 2,232,065 | 2/1941 | Hasselwander | 55/385 R |
| 2,720,013 | 10/1955 | Clarke | 416/146 R X |
| 2,790,510 | 4/1957 | Brabec | 55/385 R X |
| 2,982,524 | 5/1961 | Bland | 416/62 X |
| 3,422,263 | 1/1969 | Asahina | 416/146 R X |
| 3,645,694 | 2/1972 | Flatau | 416/146 R UX |
| 4,422,824 | 12/1983 | Eisenhardt | 416/5 |

FOREIGN PATENT DOCUMENTS 267334  6/1950  Switzerland ................... 416/146 R Primary Examiner—Everette A. Powell, Jr.
Attorney, Agent, or Firm—Joseph Zallen

[57] ABSTRACT

A method and device for reducing the pollution of the air in a room equipped with a ceiling fan having one or more rotating blades comprising covering at least one blade of the fan with porous dust-absorbent material whereby movement of the fan blades removes pollution from the room air.

15 Claims, 5 Drawing Figures

ROOM AIR CLEANER

BACKGROUND OF INVENTION

This invention relates to a room air cleaner. In particular it relates to such cleaners as used in rooms having ceiling fans.

The problem of removing dust, pollen, smoke and other air impurities has become a matter of very great concern, particularly with the increase in air pollution. In buildings which have central air conditioning systems the use of glass fiber air filters reduces interior pollution but to an unsatisfactory extent. Various self-contained small devices having thicker filters in conjunction with fans are being used in individual rooms to aid in the removal of air pollution, but their action is not sufficient to keep a room substantially free of pollution.

One object of the present invention is to provide a novel device and method for substantially decreasing air pollution in rooms equipped with ceiling fans.

Other objects and advantages of this invention will be apparent from the description and claims which follow, taken together with the appended drawings.

SUMMARY OF INVENTION

Ceiling fans which are installed in rooms are commonly provided with accessible speed controls and have blades typically ranging from three to four feet or more in length with three to four blades in the fan. In accordance with the present invention, one or more of the blades is covered with a resilient fitted cover made of woven textured material as for example, cotton, polyester, or blends thereof. Different materials remove particles at a different rate in relation to their porosity. Coating the cover with a mist of oil such as lemon oil helps in inserting or removing of the blade cover. A preferred form of cover is one where there is a layer of open weave material covered by a closely-woven material, which helps reduce noise at higher fan speeds.

The filtering action of the cover on the fan blades is effective at all speeds. In fact, the filtering action is operative even when the electric current is off and there is occasional movement of the blades by the natural movement of the air. A liquid or solid fragrance can be inserted in or under the cover. The cover has an incidental benefit of providing more safety by covering the normally sharp edges.

SPECIFIC EXAMPLES OF INVENTION

Figure 1:
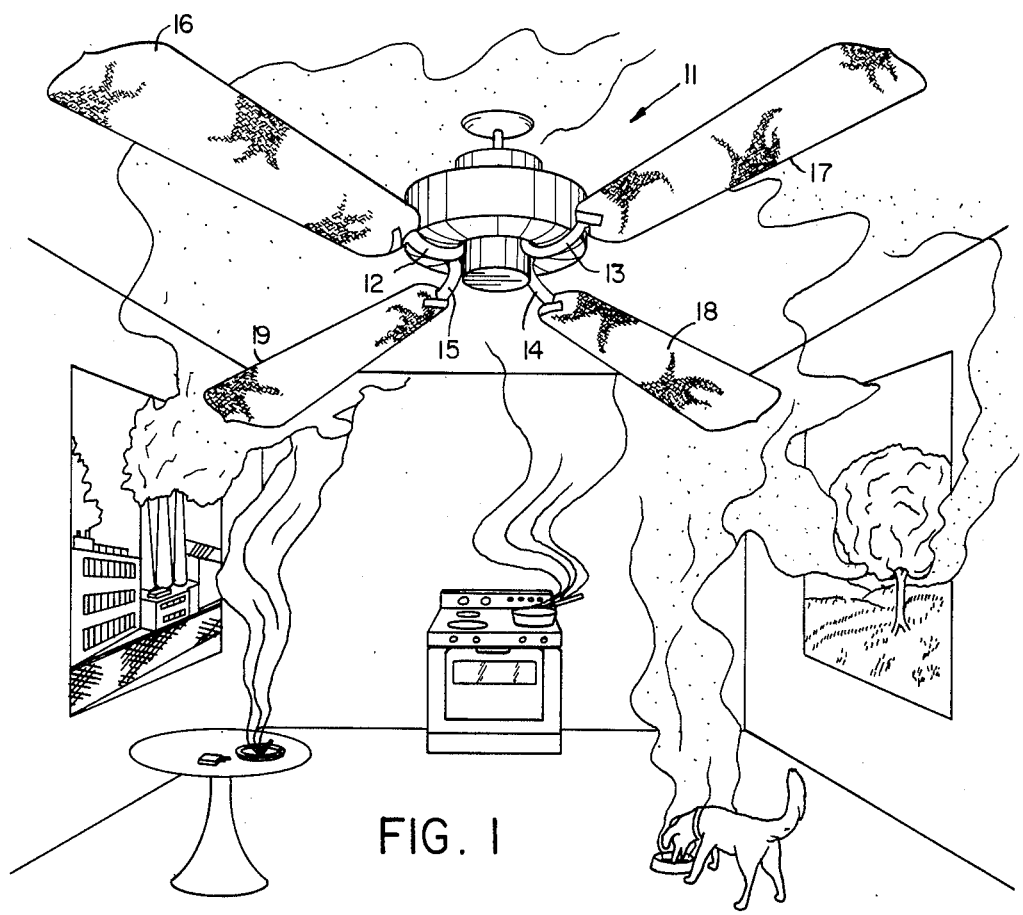
FIG. 1 is an interior perspective view of a ceiling fan having four blades each of which is covered by an embodiment of this invention.
Figure 2:
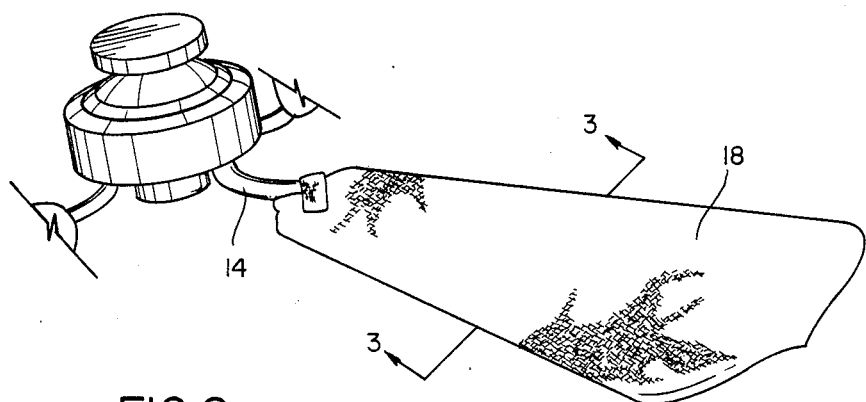
FIG. 2 is an upper perspective view of a portion of the fan.
Figure 3:
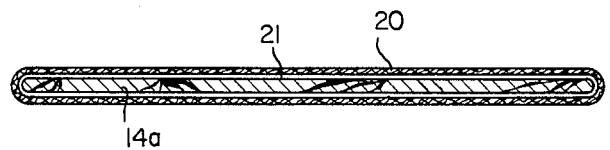
FIG. 3 is a cross section along line 3—3 of FIG. 2.
Figure 4:
FIG. 4 is a perspective view of FIG. 2 showing the cover in partially engaged position on the blade.
Figure 5:
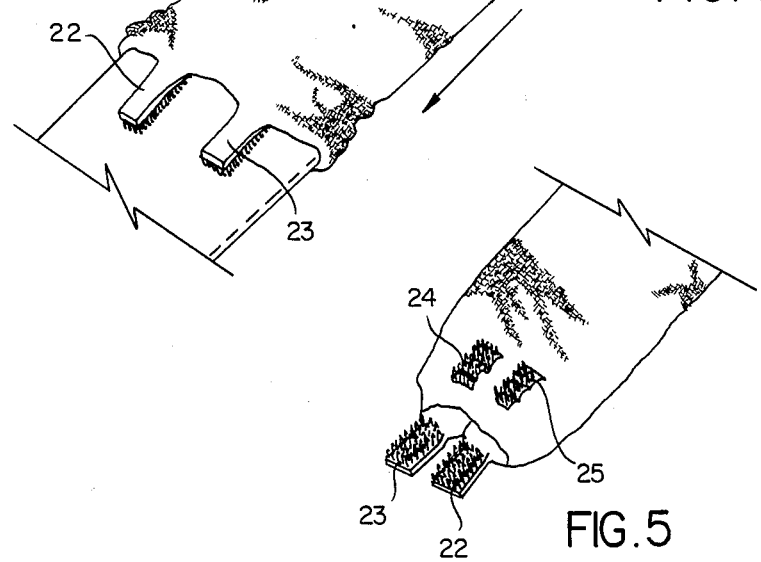
FIG. 5 is a perspective view with partial cutaway of the inner end of the cover.

Referring now to the drawings, there is illustrated therein a ceiling fan 11 in a room having a variety of man-made and natural pollution as for example, tree pollen, factory smoke, cigarette smoke, cooking odors and animal odors. Connected to the rotating mechanism of the fan are blade holders 12, 13, 14 and 15 to which are connected blades exemplified by blade 14a.

The cover 18 which is an embodiment of this invention is an outside woven layer 20 and an inside woven layer 21 both formed from elasticized material in the shape of a closed tube with an open end. The open end has elongated attachment means 22 and 23 which extend back over blade holder 14 to connect surfaces 24 and 25 on the reverse side of the cover when the cover is in position on the blade.

We claim:

1. A device for reducing the pollution of the air in a room equipped with a ceiling fan having rotating blades comprising a removable resilient cover which when fitted over such a fan blade fits snugly over substantially the entire outer surface thereof, said cover being of tubular construction with an open end and made of dust-absorbent material.

2. The device of claim 1 wherein said material comprises at least one layer of a woven fabric.

3. The device of claim 2 wherein said fabric is elasticized.

4. The device of claim 2 wherein there are two layers of woven fabric, one being tightly woven, and the other being of open weave.

5. The device of claim 1 wherein said cover has gripping means at its open end for holding it onto said blade.

6. The device of claim 1 wherein said material is coated with dust-retentive material.

7. The device of claim 5 wherein said dust-retentive material is lemon oil.

8. In combination: a ceiling fan having rotating blades and removable resilient covers fitted over such blades, so as to fit snugly over substantially the entire outer surface thereof, said covers being of tubular construction with an open end and made of dust-absorbent material.

9. The combination of claim 8 wherein said material comprises at least one layer of a woven fabric.

10. The combination of claim 9 wherein said fabric is elasticized.

11. The combination of claim 9 wherein there are two layers of woven fabric, one being tightly woven, and the other being of open weave.

12. The combination of claim 8 wherein said material is coated with dust-retentive material.

13. The combination of claim 12 wherein said dust-retentive material is lemon oil.

14. The combination of claim 8 wherein said cover has gripping means at its open end for holding it onto said blade.

15. A method for reducing the pollution of the air in a room equipped with a ceiling fan having rotating blades comprising covering substantially the entire outer surface of the blades of the fan with a removable dust-absorbent layer whereby movement of the fan blades causes said layer to remove pollution from the room air.

* * * * *